US012797510B2

(12) United States Patent
Tran et al.

(10) Patent No.: US 12,797,510 B2
(45) Date of Patent: Nov. 17, 2026

(54) CITRATE-BASED BONE GRAFTING MATERIALS

(71) Applicant: Acuitive Technologies, Inc., Allendale, NJ (US)

(72) Inventors: Minh-Tuan Richard Tran, Ho-Ho-Kus, NJ (US); Margaret Gibson, Middletown, NJ (US); Audrey Azeez, Watchung, NJ (US)

(73) Assignee: Acuitive Technologies, Inc., Allendale, NJ (US)

( * ) Notice: Subject to any disclaimer, the term of this patent is extended or adjusted under 35 U.S.C. 154(b) by 176 days.

(21) Appl. No.: 18/538,772

(22) Filed: Dec. 13, 2023

(65) Prior Publication Data

US 2024/0216574 A1 Jul. 4, 2024

Related U.S. Application Data

(60) Provisional application No. 63/432,420, filed on Dec. 14, 2022.

(51) Int. Cl.

| | |
|---|---|
| ***A61L 27/18*** | (2006.01) |
| ***A61L 27/10*** | (2006.01) |
| ***A61L 27/12*** | (2006.01) |
| ***A61L 27/56*** | (2006.01) |
| ***A61L 27/58*** | (2006.01) |
| ***C08G 63/60*** | (2006.01) |

(Continued)

(52) U.S. Cl.
CPC ............... *A61L 27/18* (2013.01); *A61L 27/10* (2013.01); *A61L 27/12* (2013.01); *A61L 27/56* (2013.01); *A61L 27/58* (2013.01); *C08G 63/60* (2013.01); *C08K 3/32* (2013.01); *C08K 9/02* (2013.01); *A61L 2400/06* (2013.01); *A61L 2400/12* (2013.01); *A61L 2430/02* (2013.01); *C08K 2003/325* (2013.01)

(58) Field of Classification Search
None
See application file for complete search history.

(56) References Cited

U.S. PATENT DOCUMENTS

2017/0080125 A1* 3/2017 Yang ........................ A61L 27/46
2020/0093770 A1* 3/2020 Yang ...................... A61K 31/80

FOREIGN PATENT DOCUMENTS

CA 3172926 A1 * 10/2021 ........... C08G 18/751

OTHER PUBLICATIONS

He, Y., et al., Development of osteopromotive poly (octamethylene citrate glycerophosphate) for enhanced bone regeneration, Acta Biomater., 93 (2019) pp. 180-191. (Year: 2019).*

(Continued)

*Primary Examiner* — Dominic Lazaro
(74) *Attorney, Agent, or Firm* — McCarter & English, LLP

(57) ABSTRACT

Grafting materials are disclosed that are fabricated from citrate-based materials. The grafting materials have particular applicability in forming a biodegradable scaffold and generally include a composition that includes (i) a citrate component, (ii) a polyol, and (iii) particulate inorganic material. The polyol may take the form of a diol, e.g., butanediol, hexanediol, octanediol, or polyethylene glycol. The scaffold may take the form of a crosslinked polymer network, may be biodegradable, and may be 50-90% porous. The scaffold may be conformable and may be adapted to be cut in an operating room.

21 Claims, 16 Drawing Sheets

(51) Int. Cl.
*C08K 3/32* (2006.01)
*C08K 9/02* (2006.01)

(56) References Cited

OTHER PUBLICATIONS

Abbasi, N., Hamlet, S., Love, R. M., & Nguyen, N.-T. (2020). Porous scaffolds for Bone Regeneration. Journal of Science: Advanced Materials and Devices, 5(1), 1-9. https://doi.org/10.1016/j.jsamd.2020.01.007.

Chen QZ, Thompson ID, Boccaccini AR. 45S5 Bioglass-derived glass-ceramic scaffolds for bone tissue engineering. Biomaterials. Apr. 2006;27(11):2414-25. doi: 10.1016/j.biomaterials.2005.11.025. Epub Dec. 5, 2005. PMID: 16336997.

Devis Bellucci, Antonella Sola, Alexandre Anesi, Roberta Salvatori, Luigi Chiarini, Valeria Cannillo, Bioactive glass/hydroxyapatite composites: Mechanical properties and biological evaluation, Materials Science and Engineering: C, vol. 51, 2015, pp. 196-205, ISSN 0928-4931, https://doi.org/10.1016/j.msec.2015.02.041.

Galow, A.-M., Rebl, A., Koczan, D., Bonk, S. M., Baumann, W., & Gimsa, J. (2017). Increased osteoblast viability at alkaline ph in vitro provides a new perspective on bone regeneration. Biochemistry and Biophysics Reports, 10, 17-25. https://doi.org/10.1016/j.bbrep.2017.02.001.

Hu, Yong-cheng; Zhong, Ji-pin Osteostimulation of bioglass, Chinese Medical Journal: Oct. 2009—vol. 122—Issue 19—p. 2386-2389 doi: 10.3760/cma.j.issn.0366-6999.2009.19.035.

Ma, C., Gerhard, E., Lin, Q., Xia, S., Armstrong, A. D., & Yang, J. (2018). In vitro cytocompatibility evaluation of poly (octamethylene citrate) monomers toward their use in orthopedic regenerative engineering. Bioactive Materials, 3(1), 19-27. https://doi.org/10.1016/j.bioactmat.2018.01.002.

Nalley, C. C., Lieberman, I. H., Morisue, H., Ferrara, L. A., & Benzel, E. C. (2017). Bone Void Fillers. Benzel's Spine Surgery, 2-Volume Set. https://doi.org/10.1016/b978-0-323-40030-5.00031-9.

Safety Data Sheet—mo-SCI corporation Mo-SCI Corporation. (n.d. ). Retrieved May 13, 2022, from https://mo-sci.com/wp-content/uploads/product-docs/biomaterials/GL0811-SDS.pdf.

Sayed Mahmood Rabiee, Neda Nazparvar, Misaq Azizian, Daryoosh Vashaee, Lobat Tayebi, Effect of ion substitution on properties of bioactive glasses: A review, Ceramics International, vol. 41, Issue 6, 2015, pp. 7241-7251, ISSN 0272-8842, https://doi.org/10.1016/j.ceramint.2015.02.140.

Tran, R. T., Yang, J., & Ameer, G. A. (2015). Citrate-Based Biomaterials and Their Applications in Regenerative Engineering. Annual review of materials research, 45, 277-310. https://doi.org/10.1146/annurev-matsci-070214-020815.

Wang, W., & Yeung, K. W. K. (2017). Bone grafts and biomaterials substitutes for bone defect repair: A review. Bioactive Materials, 2(4), 224-247. https://doi.org/10.1016/j.bioactmat.2017.05.007.

* cited by examiner

B.

CITRATE-BASED BONE GRAFTING MATERIALS

BACKGROUND

1. Cross-Reference to Related Application

The present application claims priority benefit to a US provisional patent application entitled "Citrate-Based Bone Grafting Materials," which was filed on Dec. 14, 2022, and assigned Ser. No. 63/432,420. The entire content of the foregoing US provisional patent application is incorporated herein by reference.

2. Technical Field

The present disclosure is directed to citrate-based polymer-bioceramic compositions having beneficial utility as synthetic grafts for bone regeneration applications.

3. Background Art

Currently, bone is the second most common tissue transplanted with over two million bone grafting procedures performed annually to repair bone defects. While autologous grafts are considered the gold standard for bone defect repair, there are many disadvantages associated with the use of autograft tissue. [See, Wang, W., & Yeung, K. W. K. (2017). Bone grafts and biomaterials substitutes for bone defect repair: A review. Bioactive Materials, 2(4), 224-247. https://doi.org/10.1016/j.bioactmat.2017.05.007] For example, while autografts are generally considered to be sufficiently osteoconductive, osteoinductive, and promote osteogenesis, the patient must endure secondary surgeries to dissect and extract autogenous bone. [See, Nalley, C. C., Lieberman, I. H., Morisue, H., Ferrara, L. A., & Benzel, E. C. (2017). Bone Void Fillers. Benzel's Spine Surgery, 2-Volume Set.https://doi.org/10.1016/b978-0-323-40030-5.00031-9] Major complications can occur in up to 39% of patients when extracting autologous bone. Persistent pain also exists in the donor region for up to 25% of patients. Furthermore, the quality of the autogenous bone is inconsistent because it depends on the patient's age, gender, genetics, and overall health. [See, Nalley et al.]

Many alternatives to autograft exist, including allograft tissue, decellularized extracellular matrices, and synthetic bone grafts. Allograft resources are limited and there is evidence of slower resorption of the allograft. There are also reported unwanted inflammatory responses to allograft transplantation impeding bone regeneration. Ultimately, synthetic grafts, composed of polymer-bioceramic composites, have been developed to further improve the osteoconductivity, osteoinductivity, and osteogenesis compared to allografts and decellularized matrices.

The polymer component for synthetic bone grafts has been historically restricted to thermoplastic polymers, such as polylactic acid (PLA) or polyglycolic acid (PGA). However, these polymers present slow degradation, limited cell response, a mismatch in biomechanical compliance to host tissue, and can contribute to chronic inflammation. [See, Tran, R. T., Yang, J., & Ameer, G. A. (2015). Citrate-Based Biomaterials and Their Applications in Regenerative Engineering. Annual review of materials research, 45, 277-310. https://doi.org/10.1146/annurev-matsci-070214-0208153]

To overcome the limitations of thermoplastic polymers, citrate-based biodegradable elastomers have been developed as bioenergetic synthetic grafts for bone regeneration. Citric acid is an inexpensive, nontoxic, and naturally occurring metabolic molecule that participates in bone anatomy and physiology by regulating the growth of apatite nanocrystals and cellular energy production. [See, Tran et al.] Additionally, citrate-based biomaterials contain bulk chemistry pendant carboxylic acid and hydroxyl groups that participate in polymer chain formation and improve polymer bioceramic interactions.

Effective synthetic grafts must be highly porous with an interconnected pore structure to facilitate nutrient transport, waste removal, and tissue infiltration. [See, Abbasi, N., Hamlet, S., Love, R. M., & Nguyen, N.-T. (2020). Porous scaffolds for Bone Regeneration. Journal of Science: Advanced Materials and Devices, 5(1), 1-9. https://doi.org/10.1016/j.jsamd. 2020.01.007] Currently, various methods have been developed to produce highly porous scaffolds, including freeze-drying, gas foaming, electrospinning, phase separation, 3D printing, and porogen leaching. [See, Abbasi et al.] Porogen leaching is a well-established and popular method for creating a porous structure because it is cost-effective and many porogens, such as sodium chloride, are inert and do not interfere with the biomaterial stability. Porogen leaching also allows the pore size to be easily controlled by sieving the porogen into the target size range. Sodium chloride porogens can be easily removed by submerging the construct into deionized water. Through this porogen leaching method, interconnected, highly porous scaffolds can be made without compromising the chemistry of the polymer-bioceramic composite.

SUMMARY

According to the present disclosure, highly advantageous grafting materials are fabricated from citrate-based materials. The disclosed grafting materials have particular applicability in forming a biodegradable scaffold.

In exemplary embodiments, the disclosed grafting materials comprise a composition that includes (i) a citrate component, (ii) a polyol, and (iii) particulate inorganic material. The citrate component may comprise one or more of citric acid, citrate, or an ester of citric acid. The polyol may comprise a diol, e.g., one or more of butanediol, hexanediol, octanediol, or polyethylene glycol. Other exemplary polyols contemplated according to the present disclosure include one or more of glycerol, beta-glycerol phosphate, or xylitol.

The disclosed citrate and polyol may be reacted, for example, at a 1.0:1.0 to 1.0:1.5 molar ratio, respectively, to form a telechelomer, i.e., a functionalized low molecular weight polymer. In exemplary embodiments, the polyol may comprise glycerol at 1-40 mol % of the total polyol included in the composition. In other exemplary embodiments, the polyol may comprise beta-glycerol phosphate at 1-100 mol %, and preferably 1-40 mol %, of the total polyol included in the composition. Still further, the polyol may comprise xylitol at 1-100 mol %, and preferably 1-40 mol %, of the total polyol included in the composition.

The disclosed particulate inorganic material may comprise one or more of hydroxyapatite, tricalcium phosphate, biphasic calcium phosphate, calcium carbonate, carbonated apatite, and bioglass. The particulate inorganic material may also be coated with bioglass.

The particulate inorganic material may comprise a bioceramic present in an amount between 10 and 50 wt.-% of the composition. The particulate inorganic material may comprise a bioceramic that is micro-sized or nano-sized, and/or a bioceramic that is rod-shaped.

In exemplary embodiments, a scaffold may be formed at least in part from the disclosed composition. The scaffold may be or define a crosslinked polymer network and is generally biodegradable. The scaffold may be 50-90% porous, and is generally conformable. The scaffold may be configured and adapted to be cut in an operating room.

The disclosed scaffold may be adapted to swell in liquids by 500-1500%, and may fully degrade within or between about 6-12 months in vivo. The scaffold may be microparticulate and the microparticulate scaffold may define a paste. In exemplary embodiments, one or more peptides may be conjugated to the scaffold.

Additional features, functions and benefits of the disclosed grafting materials/scaffolds will be apparent from the description which follows, particularly when read in conjunction with the associated experimental results described herein.

BRIEF DESCRIPTION OF THE FIGURES

To assist those of skill in the art in making and using the disclosed materials/compositions, reference is made to the accompanying figures, wherein.

DESCRIPTION OF EXEMPLARY EMBODIMENTS

As noted above, the presently disclosed highly advantageous grafting materials are fabricated from citrate-based materials. The disclosed grafting materials have particular applicability in forming a biodegradable scaffold. In exemplary embodiments, the disclosed grafting materials comprise a composition that includes (i) a citrate component, (ii) a polyol, and (iii) particulate inorganic material. Additional features, functions and benefits of the disclosed grafting materials/scaffolds are described herein below with reference, at least in part, to experimental results.

a. Porosity

Figure 1:
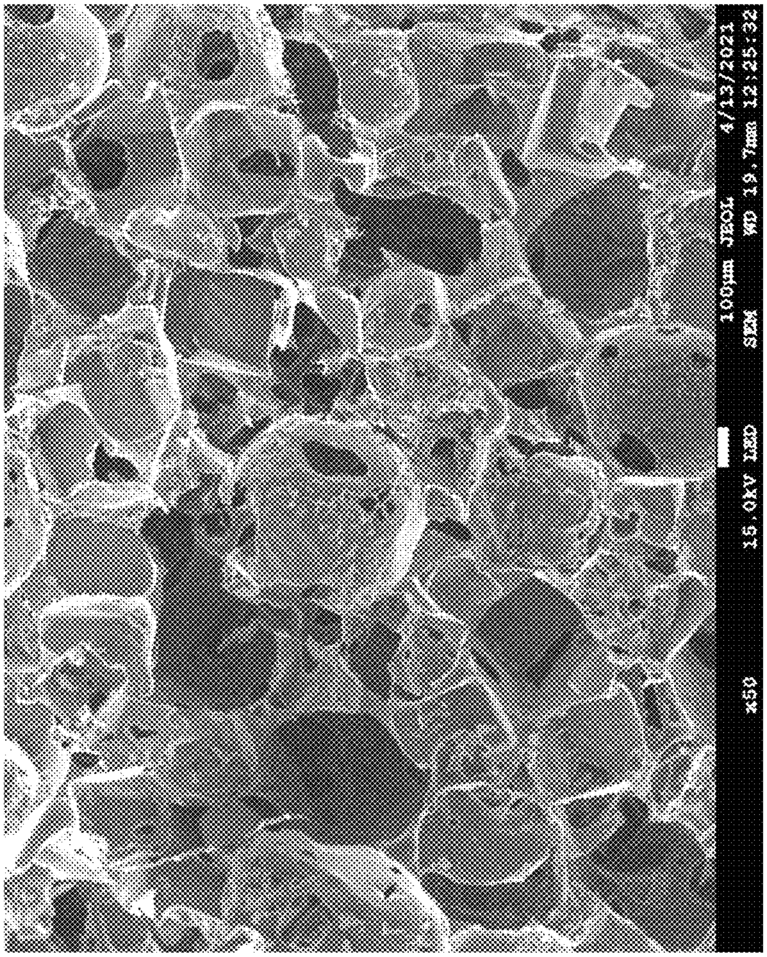
FIG. 1 is an SEM image of poly(octamethylene citrate) (POC) composited with 40 wt.-% hydroxyapatite (HA) and 92 wt.-% sodium chloride after salt leaching in deionized water.

To evaluate the porosity of biodegradable scaffolds fabricated according to the present disclosure, citrate-based polymers, such as poly(octamethylene citrate) (POC), were composited with 40 wt.-% hydroxyapatite (HA) and 92 wt.-% sodium chloride. An SEM image of the scaffold cross-section is shown in FIG. 1 displaying the porous interconnected structure.

The porosity of 92 wt.-% sodium chloride POC-HA scaffolds was further evaluated using mercury porosimetry, i.e., mercury porosimetry results of poly(octamethylene citrate) (POC) composited with 40 wt.-% hydroxyapatite and 92 wt.-% sodium chloride following salt leaching. As shown in Table 1, incorporated 92 wt.-% sodium chloride results in a scaffold with 86% porosity.

TABLE 1

| Characterization | Results |
|---|---|
| Porosity | 86.2233% |
| Total Pore Area | 0.892 $m^2/g$ |
| Average Pore Throat Diameter | 34 urn |
| Bulk Density | 0.1131 g/Ml |
| Permeability | 7914 mDa |
| Tortuosity | 9.8817 |

b. Bone Remodeling

During bone remodeling, bone tissue formation can take approximately 4 months (16 weeks). [Kenkre, J. S.; Bassett, J. H. D. (2018). The bone remodeling cycle. Annals of Clinical Biochemistry: International Journal of Laboratory Medicine, 55(3), 308-327] During this time, it is important that the degradation of the bone graft aligns with the formation of new bone as osteoblasts infiltrate and adhere to the scaffold matrix. One benefit of the disclosed citrate-based polymers is the ability to control the polymer degradation rate to meet the requirements of a specific regenerative engineering application. Since the degradation of citrate-based polymers occurs primarily through hydrolysis of the polyester, the polymer degradation rate can be fine-tuned by the hydrophobicity and hydrophilicity of the polyol used to react with citric acid (e.g., selection of aliphatic diol chain length and incorporation of hydrophilic polyols). For example, xylitol may be advantageously employed as a hydrophilic polyol according to the present disclosure.

Figure 2:
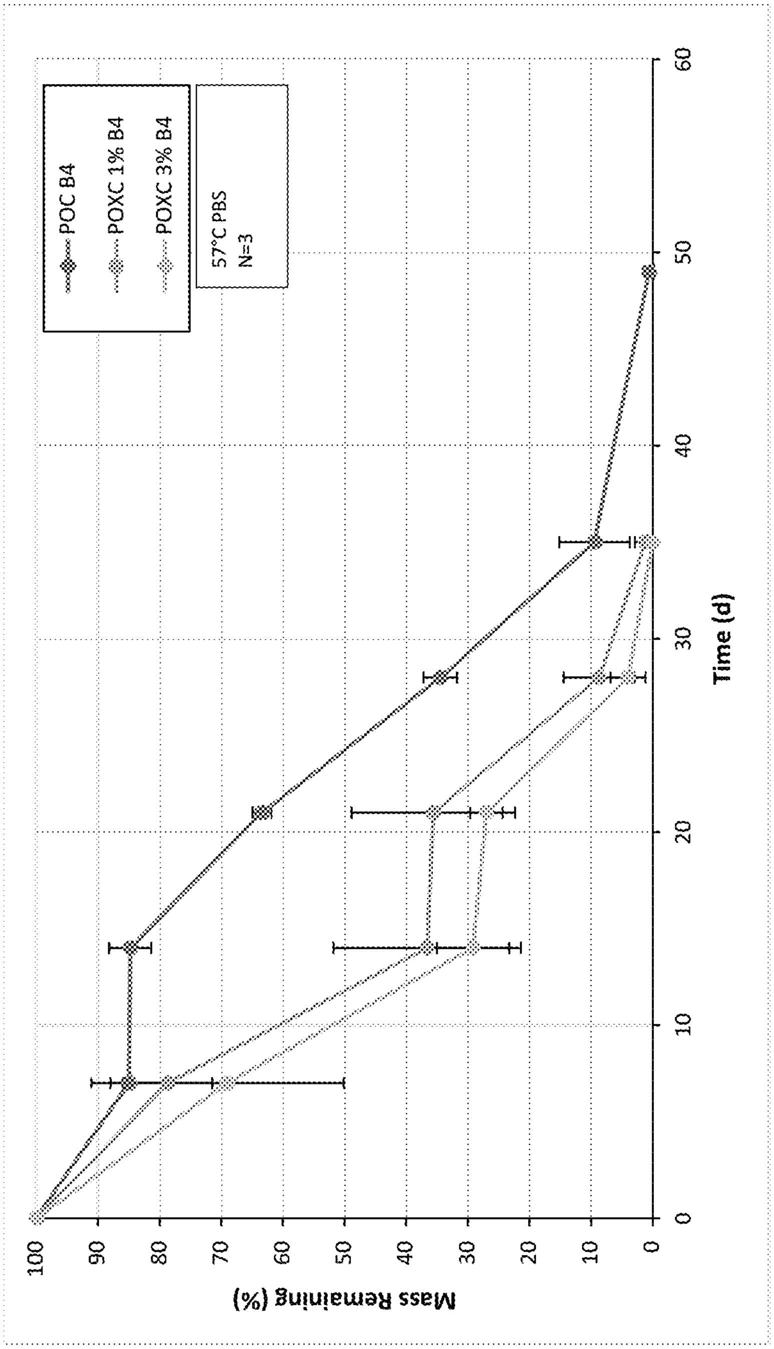
FIG. 2 is a plot showing accelerated degradation of poly(octamethylene citrate) (POC) and poly(octamethylene xylitol citrate) (POXC 3%) in 57° C. phosphate buffered saline (PBS)

As shown in FIG. 2, increasing the biomaterial hydrophilicity through the incorporation of xylitol into poly (octamethylene citrate) (POXC 1% and 3%) significantly increases the degradation rate of the resulting porous synthetic graft when compared to citrate-based grafts synthesized without xylitol (POC).

c. Bioceramics

According to the present disclosure, synthetic polymer-based grafts can be engineered to increase cell infiltration, proliferation, and differentiation by incorporating osteo-stimulative and bioactive bioceramics. Exemplary bioceramics include calcium- and phosphate-containing inorganic materials chemically similar to the mineral phase of native bone and can be used to reinforce orthopedic implants. [Mala, R.; Ruby Celsia, A. S. (2018). Bioceramics in orthopaedics: A Review. Fundamental Biomaterials: Ceramics, 195-221] Bioceramics provide structure to the scaffold architecture and have been shown to increase compressive strength and stiffness of the resulting composite. Many bioceramics are osteoconductive, which allows bone to grow on the surface of the implant. [Huang, Y.-Z., Xie, H.-Q.; Li, X. (2020). Scaffolds in Bone Tissue Engineering: Research Progress and current applications. Encyclopedia of Bone Biology, 204-215] Specifically, bioactive bioceramics are able to form hydroxyapatite mineralization on implant surfaces. Additionally, many calcium phosphate bioceramics are resorbable, causing the gradual degradation and absorption into the body, meaning surgical removal is not needed.

Hydroxyapatite (HA) is a bioceramic that has been incorporated in a wide variety of commercially available bone void fillers because it is found in the extracellular matrix of native bone tissue. Although HA is relatively bioactive when compared to inert implants, its reactivity with existing bone is low. HA implants also show relatively slow degradation, which leads to lower amounts of bone formation since the failure of HA based implants come from the fracture of the HA-bone interface. [Devis Bellucci, Antonella Sola, Alexandre Anesi, Roberta Salvatori, Luigi Chiarini, Valeria Cannillo, Bioactive glass/hydroxyapatite composites: Mechanical properties and biological evaluation, Materials Science and Engineering: C, Volume 51, 2015, Pages 196-205]

Bioglass 45S5 is an alternative bioceramic according to the present disclosure, and is widely utilized due to the many beneficial properties for bone grafts. Bioglass 45S5 is composed of 43-47% silica, 22.5-26.5% calcium oxide, 5-7% phosphorus pentoxide, and 22.5-26.5% sodium oxide, and it resorbs faster and increases the bioactivity of synthetic grafts when compared to HA. [Safety Data Sheet-mo-SCI corporation Mo-SCI Corporation. (n.d.). Retrieved May 13, 2022, from https://mo-sci.com/wp-content/uploads/product-docs/biomaterials/GL0811-SDS.pdf]

Figure 3:
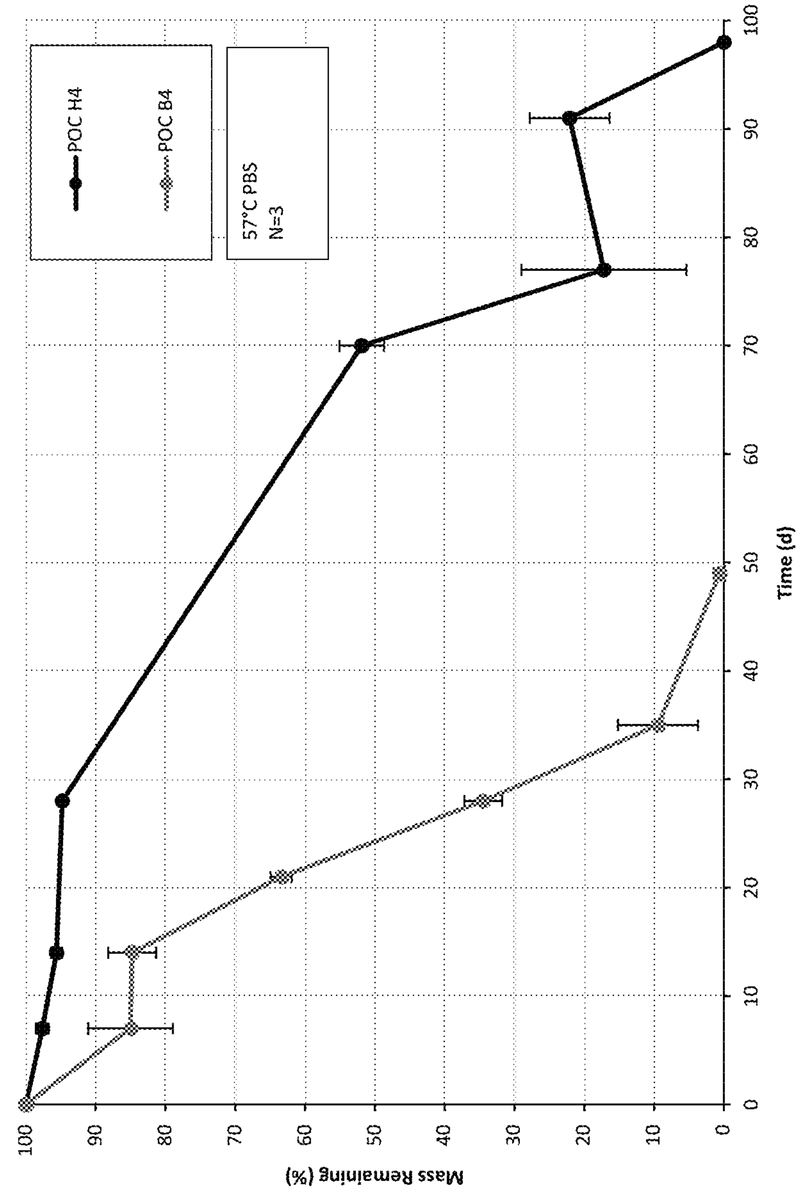
FIG. 3 is a plot showing accelerated degradation of poly(octamethylene citrate) composited with 40 wt. % hydroxyapatite (POC H4) and 40 wt. % Bioglass (POC B4) in 57° C. phosphate buffered saline (PBS) [see, Ma, C. et al., (2018). In vitro cytocompatibility evaluation of poly(octamethylene citrate) monomers toward their use in orthopedic regenerative engineering. Bioactive Materials, 3(1), 19-27]

As shown in FIG. 3, POC composites containing 40 wt.-% bioglass (POC B4) degrade significantly faster when compared to POC composites containing 40 wt.-% HA (POC H4).

In addition to a faster resorption rate, bioglass is more bioactive when compared to HA. When bioglass is hydrated in liquid, alkali ions on the surface rapidly exchange with hydrogen ions ($H^+$) from surrounding fluids. As the $H^+$ ions are exchanged, the pH of the solution subsequently increases allowing for the formation of a hydroxyl carbonated apatite (HCA) layer on the material surface mimicking the inorganic component of bone tissue. This HCA layer establishes bonds with local surrounding bone, which stimulates its growth. [Sayed Mahmood Rabiee, Neda Nazparvar, Misaq Azizian, Daryoosh Vashaee, Lobat Tayebi, Effect of ion substitution on properties of bioactive glasses: A review, Ceramics International, Volume 41, Issue 6, 2015, Pages 7241-7251]

Taking advantage of the noted pH phenomena, bioglass was composited into POC polymer in 0-40 wt.-% concentrations to determine if bioglass could buffer the acidic nature of POC polymers. ISO 10993 cytotoxicity testing was conducted on the POC-Bioglass composite scaffolds and compared POC-HA composite scaffolds fabricated using similar concentrations.

Figure 4:
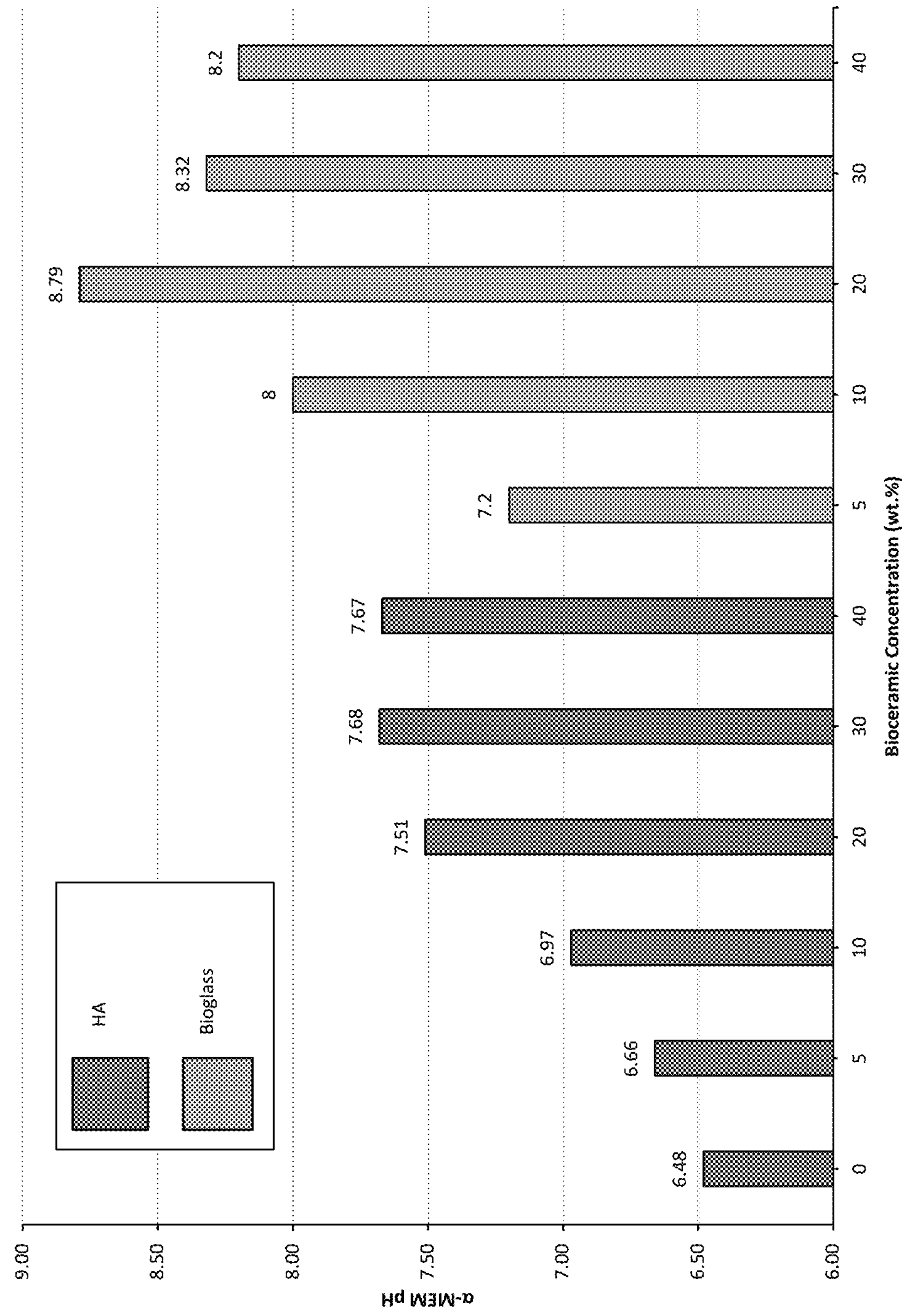
FIG. 4 is a chart showing α-MEM PH after 72 hours of leaching POC 0-40% hydroxyapatite and Bioglass.

As shown in FIG. 4, the bioglass concentrations higher than 5 wt.-% in POC scaffolds increased the extract media pH creating an alkaline environment (pH>7.4), which has been shown to promote osteoblastic differentiation and proliferation.

Figure 5:
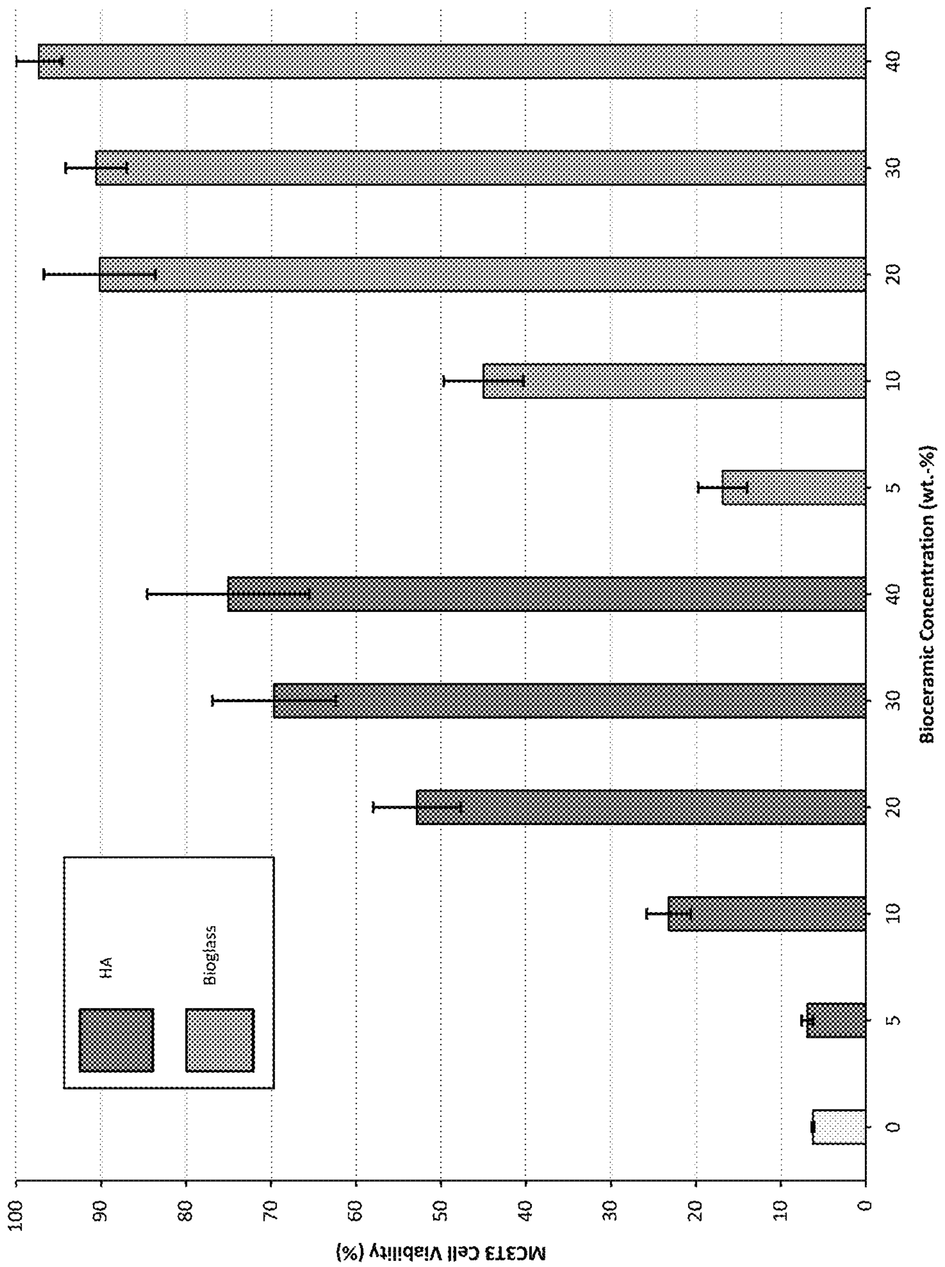
FIG. 5 is a chart showing MC3T3 mouse pre-osteoblast cell viability after exposure to extracts of POC scaffolds composited with 5-40 wt. % hydroxyapatite compared to 5-40 wt. % bioglass.

Due to the alkaline pH benefits of bioglass containing POC composites, MC3T3 mouse pre-osteoblast cell viability in response to the 72-hour $\alpha$-MEM leaching extract was over 90% when 20, 30, and 40 wt.-% Bioglass was composited into POC polymers, as shown in FIG. 5.

Bioglass also displays enhanced osteogenic and osteo-stimulative properties through increased alkaline phosphatase (ALP) production, DNA synthesis, and osteoblastic proliferation. [Hu, Yong-cheng; Zhong, Ji-pin Osteostimulation of bioglass, Chinese Medical Journal: October 2009-Volume 122-Issue 19-p 2386-2389; Chen QZ, Thompson ID, Boccaccini AR. 45S5 Bioglass-derived glass-ceramic scaffolds for bone tissue engineering. Biomaterials. 2006 Apr. 27(11):2414-25] MC3T3 mouse pre-osteoblasts were seeded onto POC composites containing bioglass and compared to hydroxyapatite composites. At a 5 wt.-% composite loading, there was not enough bioceramic to provide an osteoconductive surface for MC3T3 proliferation.

Figure 6:
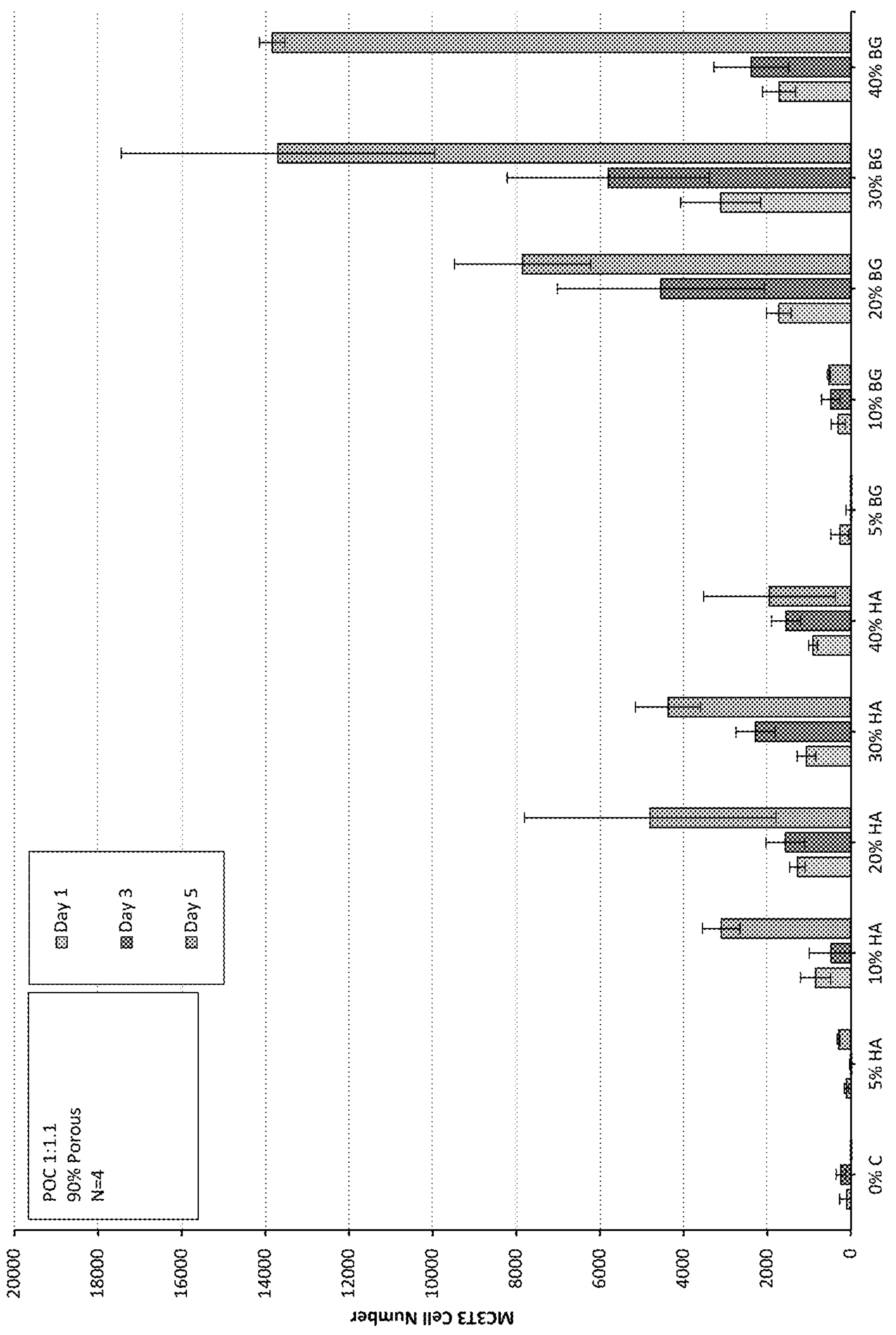
FIG. 6 is a chart showing MC3T3 mouse pre-osteoblast cell proliferation on POC scaffolds composited with 5-40 wt. % hydroxyapatite compared to 5-40 wt. % bioglass.

As shown in FIG. 6, POC composites containing 20, 30, and 40 wt.-% Bioglass allowed for significantly higher cell proliferation when compared to HA controls.

Figure 7:
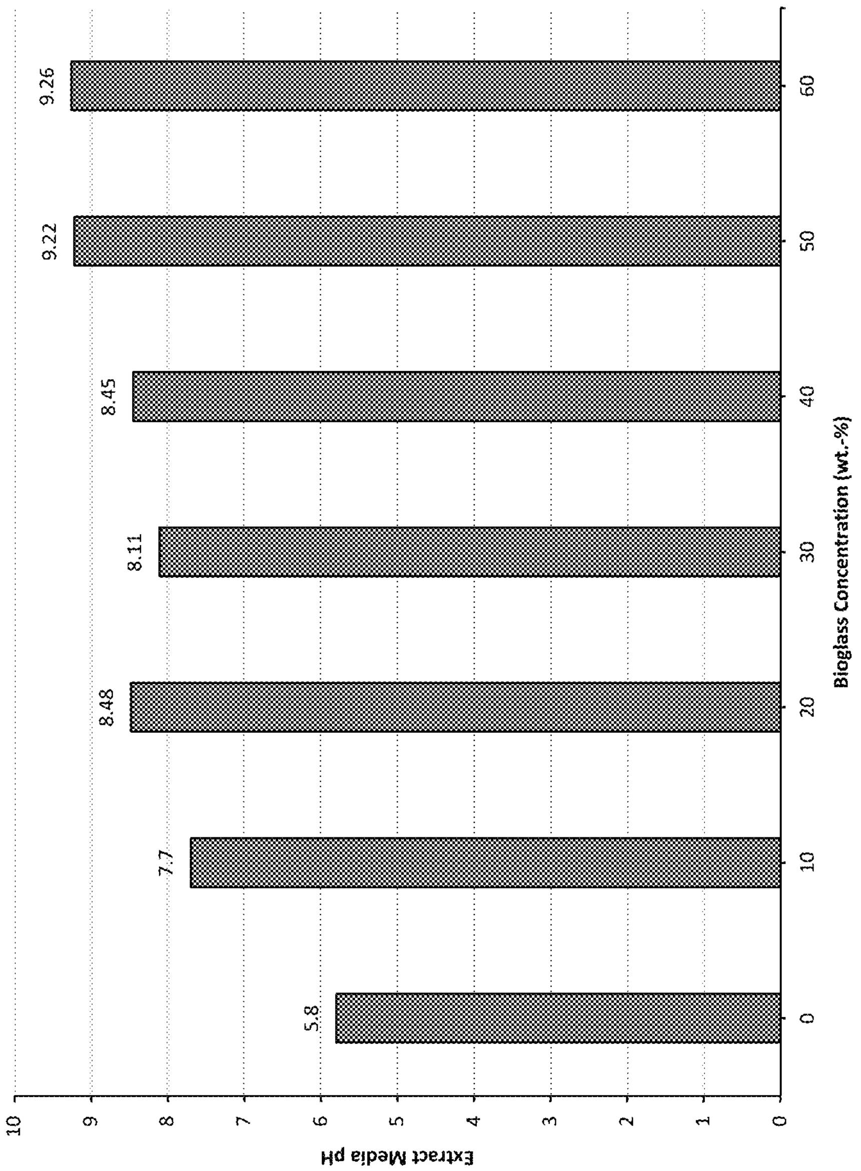
FIG. 7 is a chart showing extract media pH after 72 hours of leaching POC scaffolds containing 0-60 wt.-% Bioglass.

While increasing the bioglass concentration resulted in enhanced pre-osteoblast cell proliferation, there may be an upper limit to the bioglass concentration composited into POC. ISO 10993 cytotoxicity and cell proliferation tests were repeated using MG-63 human pre-osteoblasts on POC scaffolds containing 10-60 wt.-% (increments of 10%) bioglass. The human osteoblastic line MG-63 is useful in providing insights into cell-material interactions. Bioglass concentrations past 40 wt.-% result in extract media pH values past 9, as shown in FIG. 7.

Figure 8:
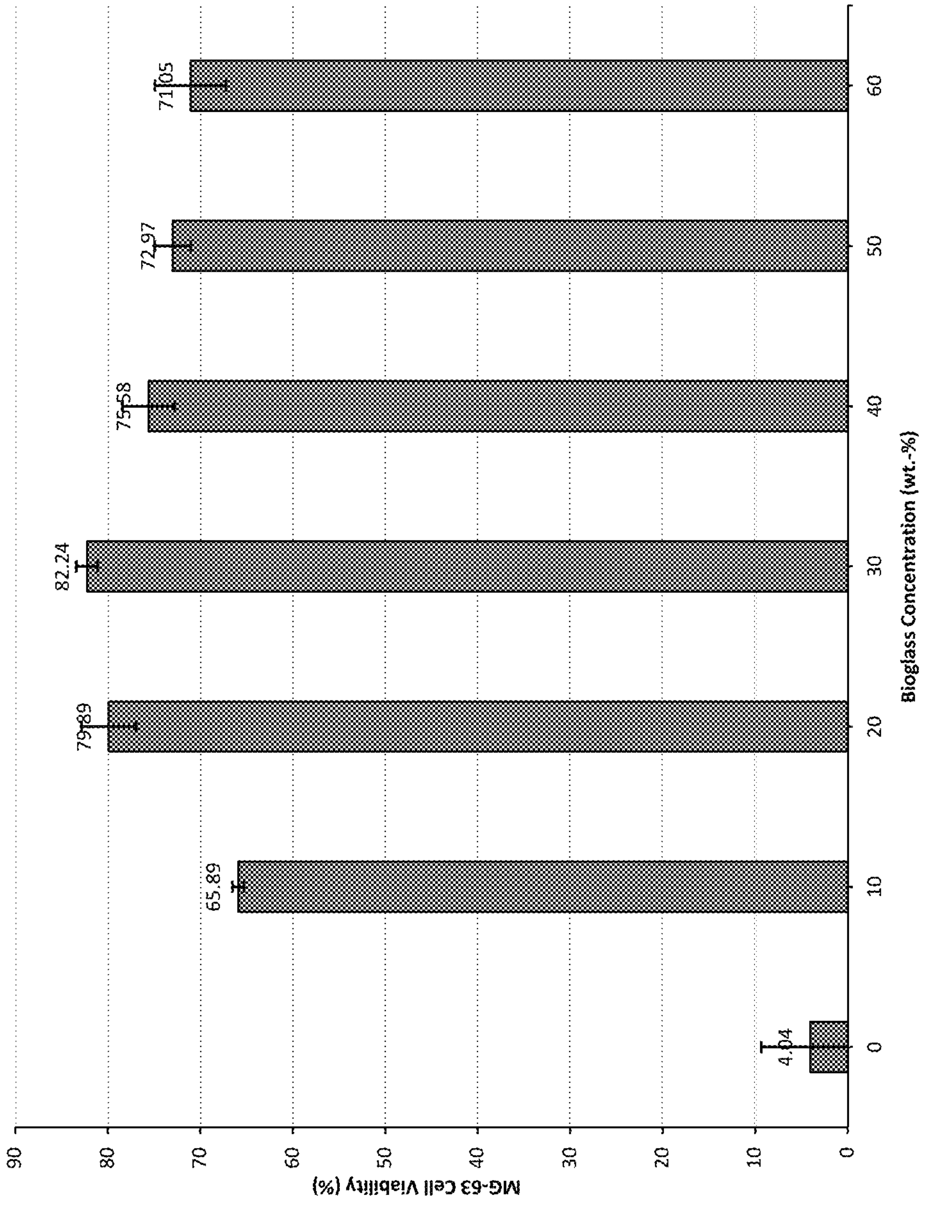
FIG. 8 is a chart showing MG-63 human pre-osteoblast cell viability after exposure to extracts of POC scaffolds composited with 10-60 wt. % bioglass.
Figure 9:
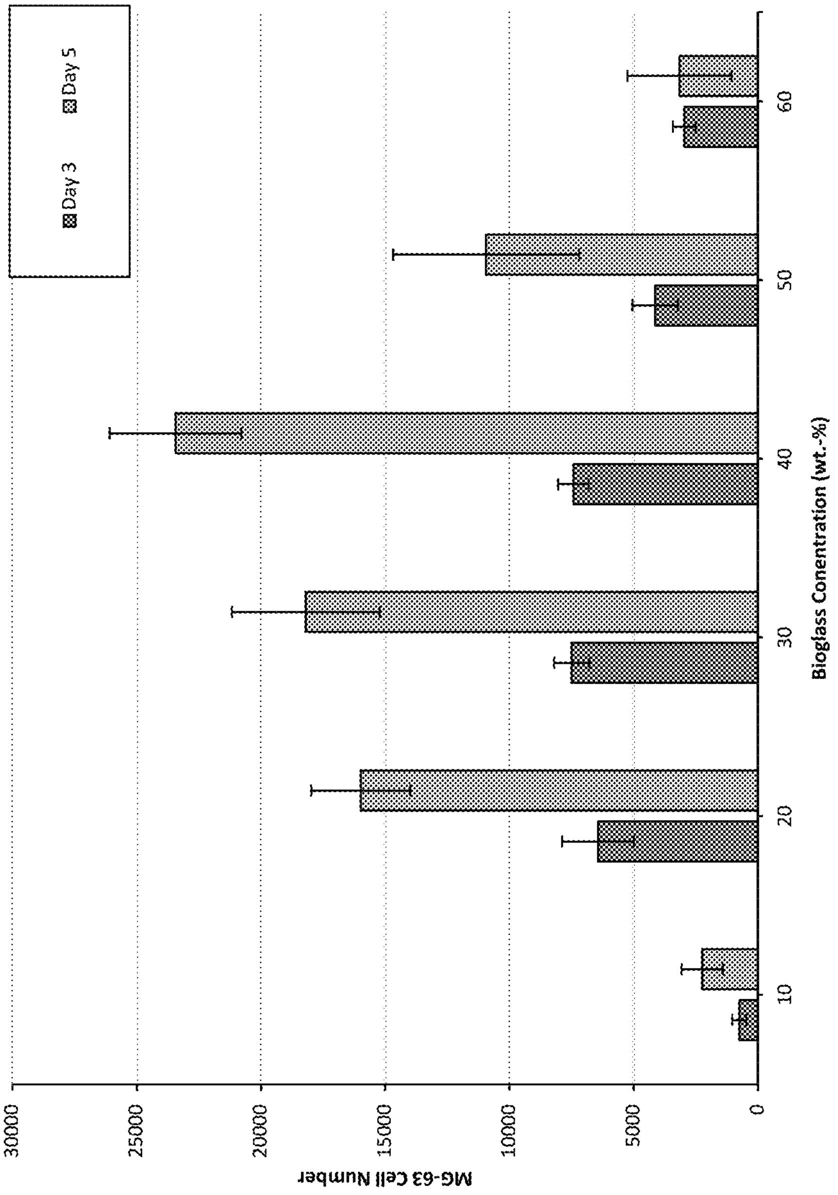
FIG. 9 is a chart showing MG-63 human pre-osteoblast cell proliferation on POC scaffolds composited with 10-60 wt. % bioglass.

Due to the elevated pH values, POC scaffolds containing bioglass concentrations higher than 40% resulted in reduced cell viability (see FIG. 8) and proliferation (see FIG. 9).

Figure 10:
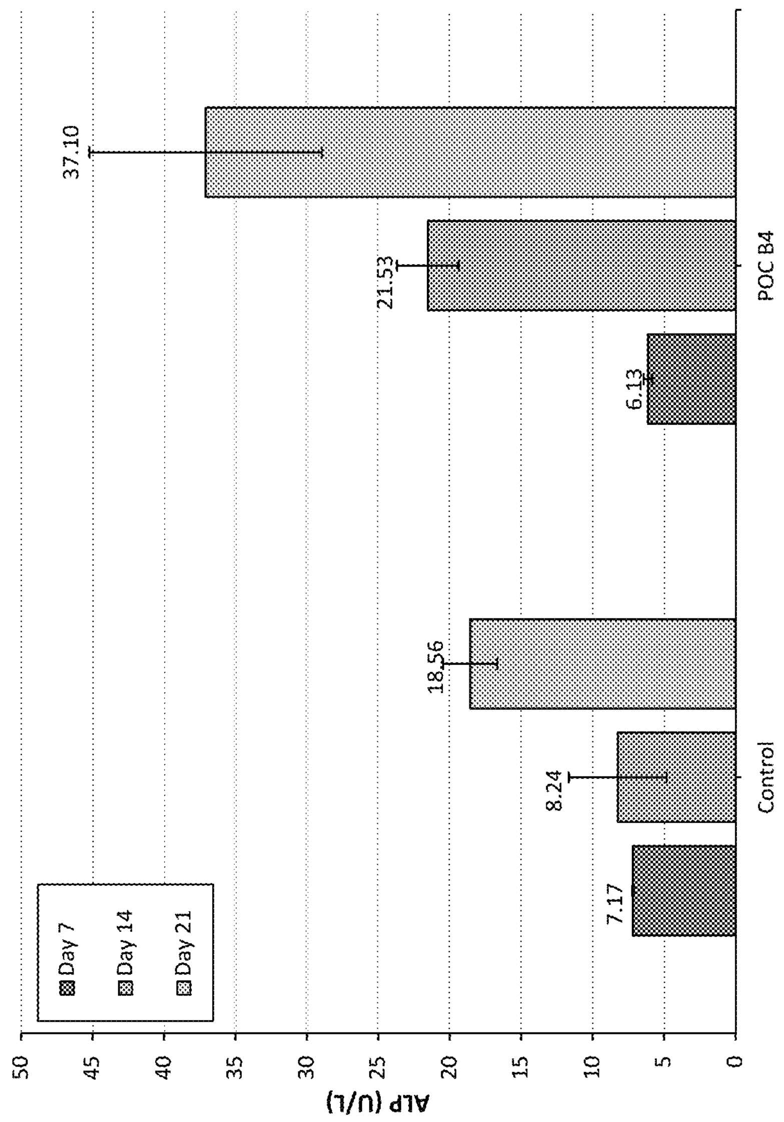
FIG. 10 is a chart showing alkaline phosphatase activity of MG-63 cells seeded on tissue control plate vs POC scaffolds composited with 40 wt. % bioglass.
Figure 11A:
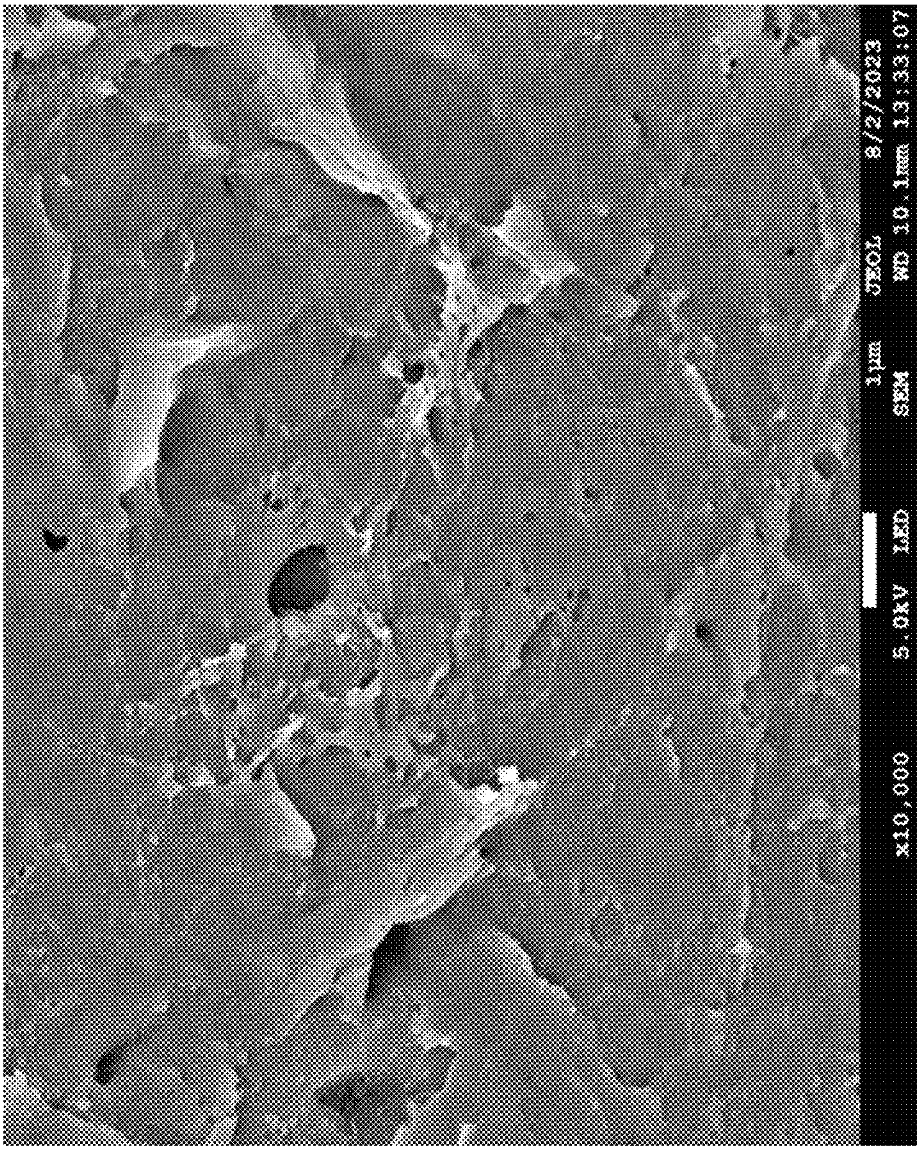
FIG. 11A is an SEM image of POC scaffolds composited with 40 wt. % bioglass before incubation in simulated body fluid.
Figure 11B:
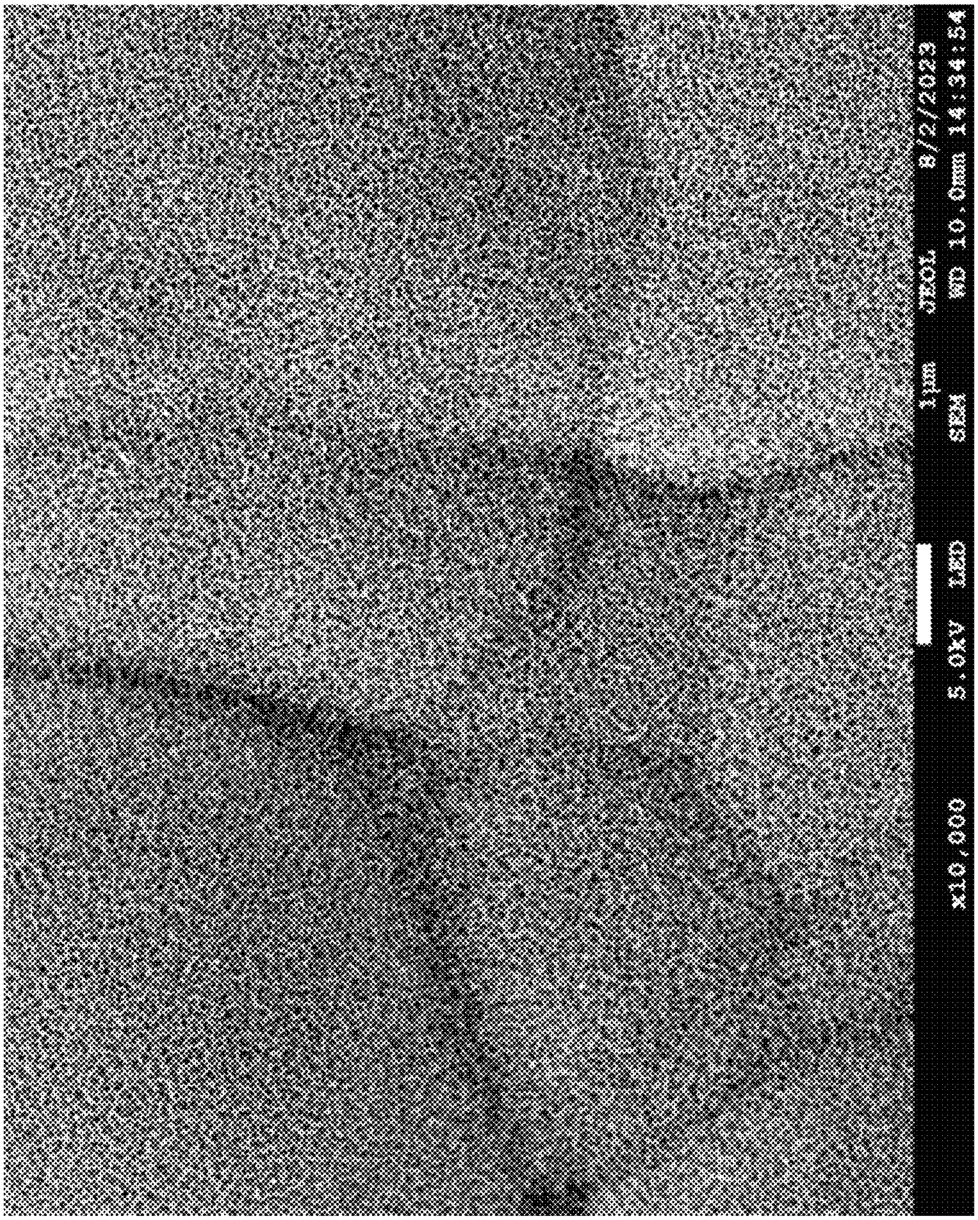
FIG. 11B is an SEM image of POC scaffolds composited with 40 wt. % bioglass seven (7) days after incubation in simulated body fluid.
Figure 12:
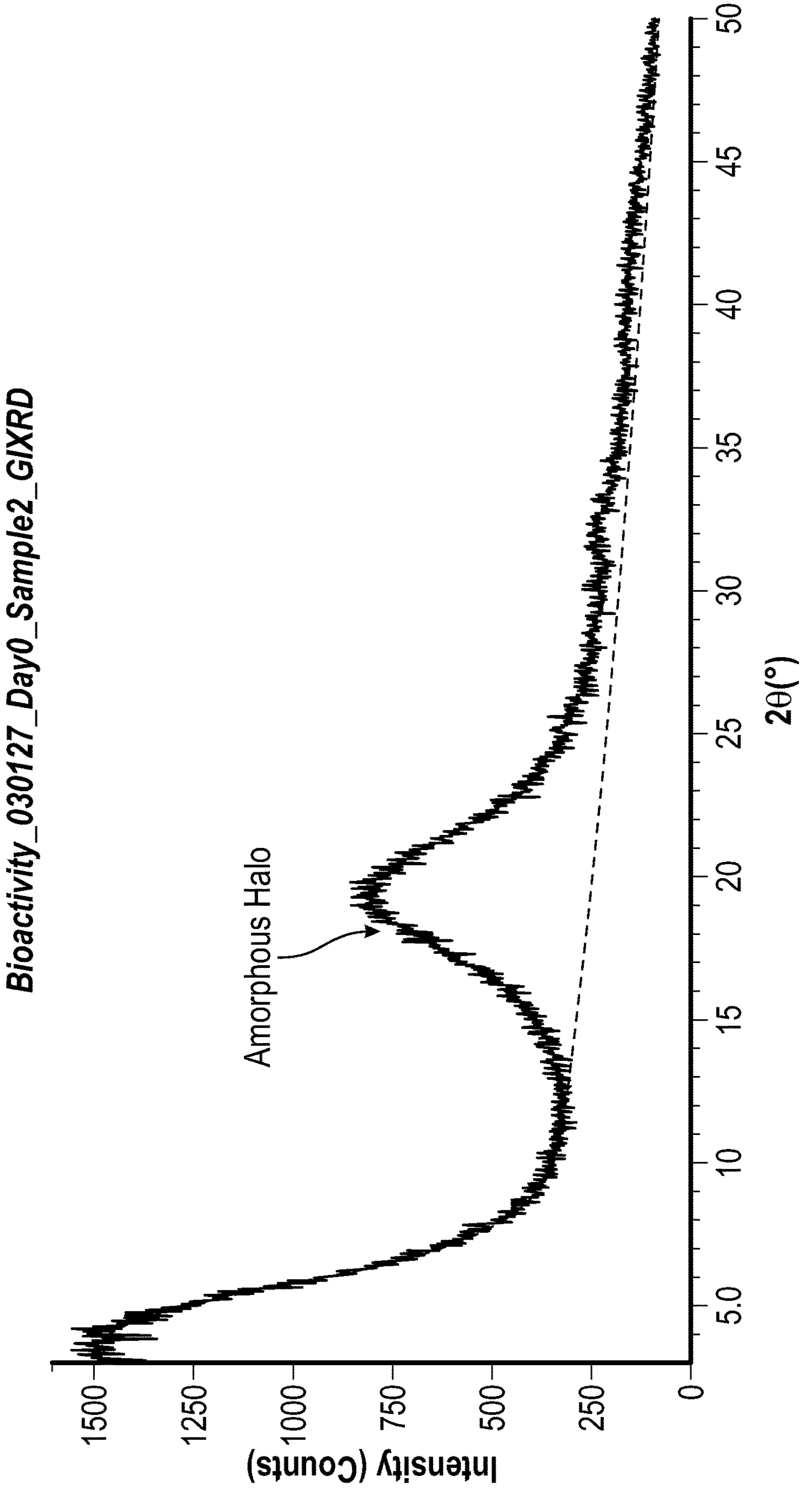
FIG. 12 is a plot showing X-ray diffraction (XRD) of POC scaffolds composited with 40 wt. % bioglass before incubation in simulated body fluid.
Figure 13:
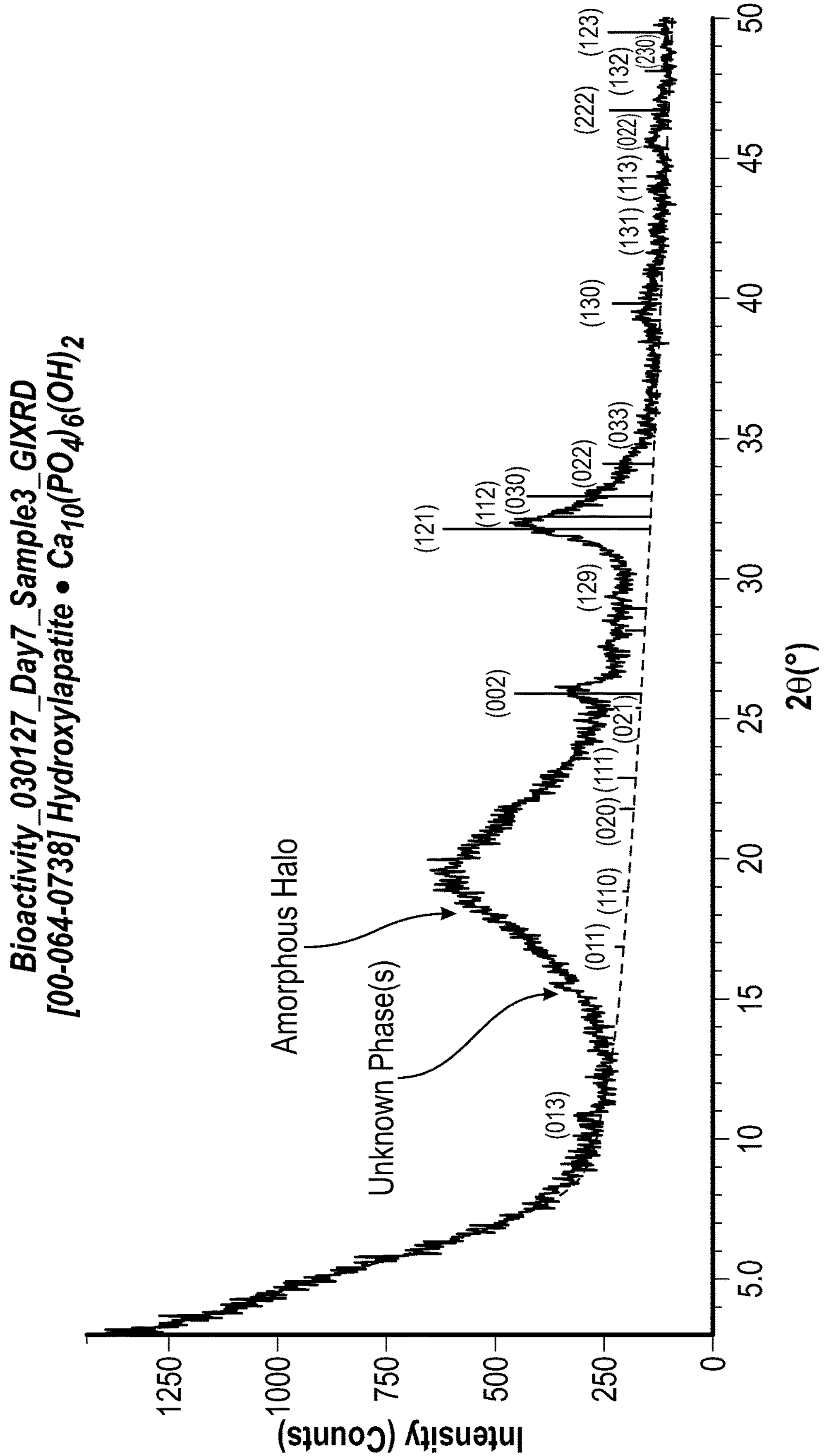
FIG. 13 is a plot showing XRD of POC scaffolds composited with 40 wt. % bioglass after seven (7) days incubation in simulated body fluid.

Based on these results, alkaline phosphatase (ALP) activity was measured for POC scaffolds with 40 wt. % bioglass to determine if the composition would increase ALP for MG63 cells compared to a tissue culture plate control. The results showed that ALP was significantly increased for the scaffolds in vitro, as shown in FIG. 10.

In vitro apatite growth was measured on POC scaffolds with 40 wt. % bioglass by SEM imaging and XRD analysis by following ISO 23317. The scaffolds were imaged and scanned before and after incubation in simulated body fluid at 37° C. The results showed the presence of apatite crystals after incubation, suggesting that the scaffolds are bioactive (see FIG. 11A, FIG. 11B, FIG. 12 and FIG. 13).

d. Scaffold Implantation

Prefabricated and easily accessible polymer-bioceramic composite grafts can also be fine-tuned to be malleable for ease of implantation and to match the mechanical properties of the native tissue. As mentioned previously, calcium phosphate bioceramics can be added to the composite to increase the compressive strength of the material. Although bioceramics alone can be brittle, when incorporated into synthetic polymers, bioceramics can improve the composite stiffness and strength. Typically, higher ceramic contents are utilized to improve the osteoconductivity of the resulting composite. However, due to the porous and interconnected structure of citrate-based synthetic grafts, increasing the bioceramic concentration can weaken the resulting construct.

Figure 14:
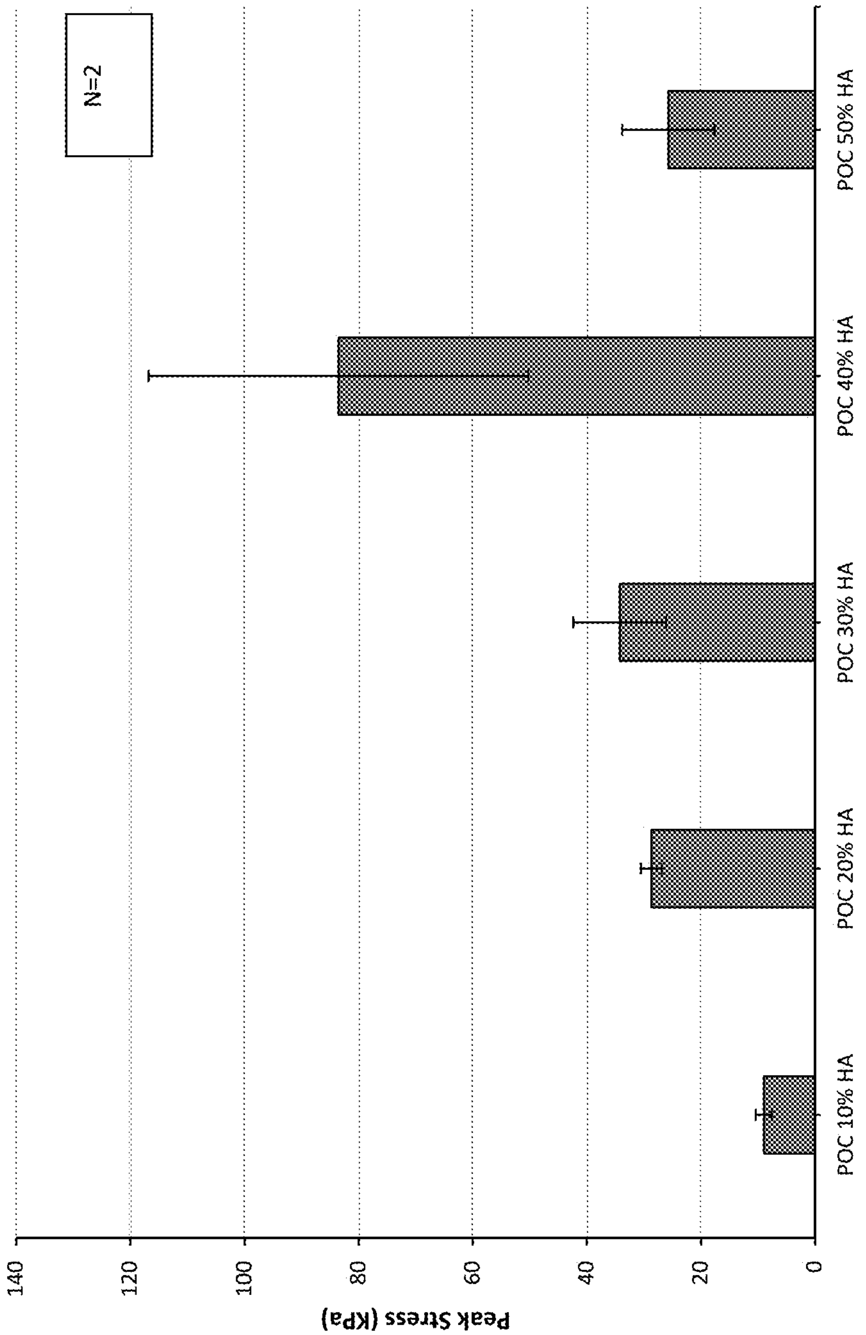
FIG. 14 is a chart showing compressive peak stress of poly(octamethylene citrate) POC porous scaffolds composited with hydroxyapatite (HA) in 10, 20, 30, 40, and 50 wt-%.

As shown in FIG. 14, the compressive peak stress of POC-HA composites peaked at 40 wt.-% HA concentrations. Increasing the HA concentration to 50 wt.-% significantly reduced the scaffold compressive peak stress.

Figure 15:
FIG. 15 is a photographic image of poly(octamethylene citrate) POC porous scaffolds composited with 60 wt.-% hydroxyapatite (HA); upon salt leaching in water, the scaffolds show brittle behavior and fall apart upon handling.

In addition, 60 wt. % hydroxyapatite scaffolds are brittle and unmalleable when fabricated into highly porous constructs and cannot function as bone void fillers as the surgeon should be able to easily handle and manipulate the material. As shown in FIG. 15, POC-HA scaffolds show a brittle behavior and fall apart immediately after salt leaching.

In exemplary embodiments of the present disclosure, the scaffold is adapted to swell in liquids by 500-1500%. In further exemplary embodiments, the scaffold fully degrades between 6-12 months in vivo.

As described herein, advantageous bone grafting materials/compositions are provided that may be advantageously employed, inter alia, in forming scaffolds. Although the present disclosure has been provided with exemplary implementations thereof, the present disclosure is not limited by or to such exemplary implementations.

The invention claimed is:

1. A composition for use as a bone grating grafting material, comprising:

a. a citrate component, b. a polyol, and c. particulate inorganic material;

wherein the particulate inorganic material comprises 43-47% silica, 22.5-26.5% calcium oxide, 5-7% phosphorous pentoxide and 22.5-26.5% sodium oxide; and wherein the particulate inorganic material comprises 20% to 40% by weight of the composition.

2. The composition of claim 1, wherein the citrate component comprises one or more of citric acid, citrate, or an ester of citric acid.

3. The composition of claim 1, wherein the polyol comprises a diol.

4. The composition of claim 3, wherein the diol comprises one or more of butanediol, hexanediol, octanediol, or polyethylene glycol.

5. The composition of claim 1, wherein the polyol comprises one or more of glycerol, beta-glycerol phosphate, or xylitol.

6. The composition of claim 1, wherein the citrate and polyol are reacted at a 1.0:1.0 to 1.0:1.5 molar ratio, respectively, to form a telechelomer.

7. The composition of claim 1, wherein the polyol comprises glycerol at 1-40 mol % of the total polyol included in the composition.

8. The composition of claim 1, wherein the polyol comprises beta-glycerol phosphate at 1-40 mol %, of the total polyol included in the composition.

9. The composition of claim 1, wherein the polyol comprises xylitol at 1-40 mol % of the total polyol included in the composition.

10. The composition of claim 1, wherein the particulate inorganic material is micro-sized or nano-sized.

11. The composition of claim 1, wherein the particulate inorganic material is rod-shaped.

12. A scaffold formed at least in part from the composition of claim 1, wherein the scaffold is a crosslinked polymer network.

13. The scaffold of claim 12, wherein the scaffold is biodegradable.

14. The scaffold of claim 12, wherein the scaffold is 50-90% porous.

15. The scaffold of claim 12, wherein the scaffold is conformable.

16. The scaffold of claim 12, wherein the scaffold is configured and adapted to be cut in an operating room.

17. The scaffold of claim 12, wherein the scaffold is adapted to swell in liquids by 500-1500%.

18. The scaffold of claim 12, wherein the scaffold fully degrades between 6-12 months in vivo.

19. The scaffold of claim 12, wherein the scaffold is microparticulate.

20. The scaffold of claim 19, wherein the microparticulate scaffold is paste.

21. The scaffold of claim 12, further comprising a peptide conjugated to the scaffold.

* * * * *